United States Patent [19]
Serbiak et al.

[11] Patent Number: 5,846,232
[45] Date of Patent: *Dec. 8, 1998

[54] ABSORBENT ARTICLE CONTAINING EXTENSIBLE ZONES

[75] Inventors: Paul John Serbiak, Appleton; Duane Girard Uitenbroek, Little Chute, both of Wis.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 575,310

[22] Filed: Dec. 20, 1995

[51] Int. Cl.⁶ .................................................. A61F 13/15
[52] U.S. Cl. ........................................ 604/385.2; 604/373
[58] Field of Search ........................... 604/385.1, 385.2, 604/373, 372, 386, 387

[56] References Cited

U.S. PATENT DOCUMENTS

| | | | |
|---|---|---|---|
| 4,500,316 | 2/1985 | Damico | 604/389 |
| 4,515,595 | 5/1985 | Kievit et al. | 604/385 |
| 4,522,874 | 6/1985 | Pommez | 428/284 |
| 4,568,344 | 2/1986 | Suzuki et al. | 604/389 |
| 4,610,681 | 9/1986 | Strohbeen et al. | 604/396 |
| 4,642,819 | 2/1987 | Ales et al. | 2/400 |
| 4,645,501 | 2/1987 | Teed | 604/390 |
| 4,661,102 | 4/1987 | Shikata et al. | 604/385 |
| 4,670,012 | 6/1987 | Johnson | 604/390 |
| 4,681,580 | 7/1987 | Reising et al. | 604/385 |
| 4,699,620 | 10/1987 | Bernardin | 604/385 |
| 4,699,621 | 10/1987 | Stevens et al. | 604/385 |
| 4,701,170 | 10/1987 | Wilson et al. | 604/385 |
| 4,701,171 | 10/1987 | Boland et al. | 604/385 |
| 4,701,172 | 10/1987 | Stevens | 604/385 |
| 4,701,173 | 10/1987 | Zehner et al. | 604/385 |
| 4,701,174 | 10/1987 | Johnson | 604/385 |
| 4,701,175 | 10/1987 | Boland et al. | 604/385 |
| 4,701,176 | 10/1987 | Wilson et al. | 604/385 |
| 4,704,114 | 11/1987 | Wilson et al. | 604/385 |
| 4,718,900 | 1/1988 | Boland et al. | 604/385 |
| 4,726,807 | 2/1988 | Young et al. | 604/385 |
| 4,747,846 | 5/1988 | Boland et al. | 604/385 |

(List continued on next page.)

FOREIGN PATENT DOCUMENTS

| | | |
|---|---|---|
| 0321985 | 6/1989 | European Pat. Off. . |
| 432763A1 | 6/1991 | European Pat. Off. . |
| 650714A1 | 5/1995 | European Pat. Off. . |
| WO9216371 | 10/1992 | WIPO . |
| WO9519753 | 7/1995 | WIPO . |
| WO9627352 | 9/1996 | WIPO . |

*Primary Examiner*—Mark O. Polutta
*Attorney, Agent, or Firm*—Thomas D. Wilhelm; Brian R. Tumm; Jeffrey B. Curtin

[57] ABSTRACT

An absorbent article includes extensible zones. These extensible zones enable the absorbent article to expand and fit a broad size range of users. The extensible zones enable a broad range of adjustment in waist and leg opening dimensions by extension and retraction of the extensible zones. The bodyside liner layer and the outer cover layer preferably comprise spunbonded layers stretched in one direction and correspondingly narrowed in another direction. The extensible zones typically include an elastic layer between, and mounted to extend with, the outer cover layer and the bodyside liner layer. The elastic layer can comprise an elastic film or strands of material. An absorbent core is located between the bodyside liner layer and the outer cover layer. A method for forming an absorbent article is also disclosed which includes the step of forming a base structure by attaching the extensible bodyside liner layer to an extensible outer cover layer and creating at least one extensible zone by incorporating the elastic layer between the outer cover layer and the bodyside liner layer. In another embodiment of the invention, a plurality of extensible zones are formed with plural elastic layer elements. In another embodiment of the invention, the outer cover layer is formed by a nonextensible layer which is gathered and attached to the elastic layer and the bodyside liner layer. In yet another embodiment of the invention, the extensible zones are formed by the outer cover layer and bodyside liner layer with no elastic layer present.

59 Claims, 6 Drawing Sheets

U.S. PATENT DOCUMENTS

| | | | |
|---|---|---|---|
| 4,753,646 | 6/1988 | Enloe | 604/385 |
| 4,753,650 | 6/1988 | Williams | 604/389 |
| 4,756,709 | 7/1988 | Stevens | 604/385 |
| 4,770,656 | 9/1988 | Proxmire et al. | 604/393 |
| 4,801,298 | 1/1989 | Sorenson et al. | 604/384 |
| 4,808,176 | 2/1989 | Kielpikowski | 604/385.2 |
| 4,808,178 | 2/1989 | Aziz et al. | 604/385.2 |
| 4,826,499 | 5/1989 | Ahr | 604/389 |
| 4,834,736 | 5/1989 | Boland et al. | 604/385.2 |
| 4,834,738 | 5/1989 | Kielpikowski et al. | 604/385.2 |
| 4,834,741 | 5/1989 | Sabee | 604/385.2 |
| 4,834,742 | 5/1989 | Wilson et al. | 604/389 |
| 4,838,885 | 6/1989 | Bernardin | 604/385.1 |
| 4,842,596 | 6/1989 | Kielpikowski et al. | 604/385.2 |
| 4,846,825 | 7/1989 | Enloe et al. | 604/385.1 |
| 4,850,990 | 7/1989 | Huntoon et al. | 604/385.2 |
| 4,850,992 | 7/1989 | Amaral et al. | 604/389 |
| 4,857,067 | 8/1989 | Wood et al. | 604/389 |
| 4,872,871 | 10/1989 | Proxmire et al. | 604/394 |
| 4,883,481 | 11/1989 | Blanchard | 604/385.1 |
| 4,892,598 | 1/1990 | Stevens et al. | 156/91 |
| 4,895,569 | 1/1990 | Wilson et al. | 604/386 |
| 4,908,247 | 3/1990 | Baird et al. | 428/34.9 |
| 4,911,702 | 3/1990 | O'Leary et al. | 604/389 |
| 4,917,682 | 4/1990 | Lancaster et al. | 604/385.2 |
| 4,937,887 | 7/1990 | Schreiner | 2/402 |
| 4,961,737 | 10/1990 | Orlando | 604/385.2 |
| 4,968,313 | 11/1990 | Sabee | 604/385.2 |
| 4,988,346 | 1/1991 | Pfefferkorn | 604/389 |
| 5,037,416 | 8/1991 | Allen et al. | 604/385.1 |
| 5,055,103 | 10/1991 | Nomura et al. | 604/385.2 |
| 5,064,421 | 11/1991 | Tracy | 604/385.1 |
| 5,066,289 | 11/1991 | Polski | 604/389 |
| 5,069,678 | 12/1991 | Yamamoto et al. | 604/385.1 |
| 5,074,854 | 12/1991 | Davis | 604/385.1 |
| 5,080,658 | 1/1992 | Igaue et al. | 604/385.2 |
| 5,092,861 | 3/1992 | Nomura et al. | 604/385.2 |
| 5,092,862 | 3/1992 | Muckenfuhs et al. | 604/385.2 |
| 5,143,679 | 9/1992 | Weber et al. | 264/288.8 |
| 5,151,092 | 9/1992 | Buell et al. | 604/385.2 |
| 5,156,793 | 10/1992 | Buell et al. | 264/288.8 |
| 5,163,932 | 11/1992 | Nomura et al. | 604/385.2 |
| 5,167,897 | 12/1992 | Weber et al. | 264/288.8 |
| 5,171,236 | 12/1992 | Dreier et al. | 604/369 |
| 5,226,992 | 7/1993 | Morman | 156/62.4 |
| 5,234,423 | 8/1993 | Alemany et al. | 604/385.2 |
| 5,376,198 | 12/1994 | Fahrenkrug et al. | 156/164 |
| 5,389,095 | 2/1995 | Suzuki et al. | 604/385.2 |
| 5,429,629 | 7/1995 | Latimer et al. | 604/378 |
| 5,575,783 | 11/1996 | Clear et al. | 604/385.2 |
| 5,611,790 | 3/1997 | Osborn, III et al. | 604/391 | ns
ABSORBENT ARTICLE CONTAINING EXTENSIBLE ZONES

BACKGROUND OF THE INVENTION

1. Technical Field

This invention pertains to an absorbent article for containing exudates. Such absorbent articles generally utilize leg elastics and waist elastics to help prevent leakage of body exudates.

2. Description of the Related Art

Absorbent articles such as infant diapers, training pants, adult incontinence products, and the like are well known. Such articles have achieved a wide acceptance due to their ability to receive and absorb body exudates.

The prior art has considered various ways and methods to make absorbent articles fit better upon a variety of users. For example, U.S. Pat. No. 4,756,709 to Stevens discloses a form-fitting self-adjusting disposable garment with a stretchable outer cover. While the outer cover is stretchable, the bodyside liner is not. The outer cover is prestretched before being mounted to the bodyside liner.

U.S. Pat. No. 4,704,114 to Wilson et al. is similar to U.S. Pat. No. 4,756,709 described above, except the garment is resiliently stretchable in two directions.

U.S. Pat. No. 4,857,067 to Wood et al. discloses a disposable diaper with shirred ears and a heat elasticizable material which allow portions of the diaper to stretch. The backsheet and topsheet of the diaper of Wood et al. both comprise nonextensible materials.

SUMMARY OF THE INVENTION

This invention relates to an absorbent article designed to absorb body exudates. The absorbent article includes extensible zones which allow the absorbent article to better fit a user'body. The absorbent article fits a wider range of users because of the extensible zones.

In one aspect the present invention resides in an absorbent article having a front portion, a rear portion, and a crotch portion connecting the front and rear portions, and a first outer perimeter, the front, rear and crotch portions, in combination, defining the overall area of the absorbent article, a longitudinal axis extending through the front, rear and crotch portions and defining a first direction in the absorbent article aligned substantially with the longitudinal axis and a respective second cross direction, the absorbent article comprising an outer cover layer formed by a first material extensible in at least one of the first direction and the second cross direction; a bodyside liner layer formed by a second material extensible in at least one of the first direction and the cross direction, the bodyside liner layer and the outer cover layer forming, in combination, a base structure; at least one elastic layer element having a second outer perimeter, defining an elastic layer between the outer cover layer and the bodyside liner layer, attached to at least one of the outer cover layer and the bodyside liner layer, wherein the outer cover layer, bodyside liner layer, and elastic layer can simultaneously coexist in a substantially fully extended unstressed condition; and at least one extensible zone, defined within the second outer perimeter of the elastic layer element and comprehending coextensive portions of the bodyside liner layer and the outer cover layer, the extensible zone allowing a broad range of extensibility of the absorbent article within the extensible zone by extension and retraction of the absorbent article in the extensible zone.

The absorbent article may further comprise an attachment element located in the rear portion, the attachment element cooperating in securing the absorbent article upon a user, the attachment element extending outwardly from respective edges of the rear portion of the absorbent article, at least one extensible zone being located in the rear portion of the absorbent article adjacent to and extending inwardly from the attachment element, the absorbent article including a nonextensible absorbent core between the bodyside liner layer and the elastic layer, the base structure being effectively fixedly attached to the absorbent core over an area of the base structure whereby the base structure is not extensible over the respective area of the base structure controlled by attachment to the absorbent core. Where the base structure is attached to the absorbent core, the remainder of the base structure can be extensible and comprise the extensible zone.

In another aspect of the invention, the extensible material of the bodyside liner layer comprises a spunbonded layer stretched in one of the first direction and the second cross direction by about 25% to about 150%, and correspondingly narrowed in the other of the first direction and the second cross direction. The extensible material of the outer cover layer can comprise the same material as the bodyside layer. The extensible material of the outer cover layer is selected from one or more of the group consisting of a spunbonded material, a spunbonded laminate such as spunbonded melt-blown spunbonded material, and a bonded carded web. The material of the bodyside liner layer can also be selected from the same group of materials. The extensible materials, of both the bodyside liner layer and the outer cover layer, can be narrowed in the cross direction, by stretching in the first direction and corresponding necking in the second cross direction, the extensible zone being extensible in the cross direction. Both the bodyside liner layer and the outer cover layer can be creped such that the creping is extensible in the first direction, so that the absorbent article is extensible in the extensible zone in both the first direction and the second cross direction. The absorbent article can also be extensible only in the first direction or only in the second cross direction with respect to the extensible zone.

In another aspect of the invention the elastic layer comprises strands of elastic material or a film. The elastic layer can be disposed only in common with the extensible zone or the elastic layer can extend between the outer cover layer and the bodyside liner layer over as much as all of the overall area defined by the absorbent article.

In one embodiment of the invention first and second extensible zones are formed in the rear portion of the absorbent article, first and second attachment elements being disposed on opposing sides of the rear portion and adjacent the first and second extensible zones, the rear portion of the absorbent article including a second elastic layer element in the second extensible zone, the first and second elastic layer elements being disposed between respective ones of the attachment elements and the absorbent core.

In another embodiment of the invention, the absorbent article comprises an extensible zone in the rear portion and in the crotch portion, the base structure thereby having extensible properties in the rear portion, and in the crotch portion adjacent the rear portion and extending to a narrowest part of the crotch portion, an absorbent core disposed between the outer cover layer and the bodyside liner layer and extending from within the front portion, through the crotch portion to within the rear portion, the absorbent core being free from fixed attachment to the base structure over a substantial area of the rear portion of the absorbent article, coextensive with the absorbent core, whereby the base structure is extensible in the rear portion independent of the absorbent core. Further, a second extensible zone in the front portion of the absorbent article can be formed, the second extensible zone extending from a central region across a front edge of the front portion inwardly into the front portion.

In another embodiment of the invention the absorbent article has a base structure which is extensible in extensible zones on opposing sides of the absorbent article in the front portion and the rear portion of the absorbent article, the absorbent article not being extensible in a central region of the absorbent article extending along the longitudinal axis and having a width narrower than a minimum width of the absorbent article.

In another embodiment of the invention the absorbent article has a base structure extensible in a central extensible zone extending along the longitudinal axis and having a width narrower than a minimum width of the absorbent article, the absorbent article including an absorbent core received between the outer cover layer and the bodyside liner layer, in the front, crotch and rear portions of the absorbent article, the absorbent core being without effective securement to either of the outer cover layer or the bodyside liner layer about the central extensible zone.

In another embodiment of the invention the base structure is extensible in an extensible zone comprising the crotch portion of the absorbent article. The crotch portion can include leg elastics spaced outwardly from the longitudinal axis, wherein the leg elastics can coexist simultaneously with the base structure in substantially fully extended unstressed condition, the leg elastics extending when the base structure is extended in the extensible zone in the first direction.

In another aspect of the invention, at least one substantially nonextensible layer element is attached to the base structure. The nonextensible layer element forms a nonextensible region even in the presence of an elastic layer.

Another aspect of the invention comprises an absorbent article having a front portion, a rear portion, a crotch portion connecting the front and rear portions, and a first outer perimeter, the front portion, the rear portion, and the crotch portion, in combination, defining an overall area of the absorbent article, a longitudinal axis extending through the front, rear and crotch portions and defining a first direction in the absorbent article aligned with the longitudinal axis, and a respective second cross direction, the absorbent article comprising an outer cover layer formed by a substantially nonextensible first material; a bodyside liner layer formed by a second material extensible in at least one of the first direction and the second cross direction, the bodyside liner layer and the outer cover layer forming, in combination, a base structure; at least one elastic layer element having a second outer perimeter, defining an elastic layer between the outer cover layer and the bodyside liner layer, attached to at least one of the outer cover layer and the bodyside liner layer; and at least one extensible zone, defined within the second outer perimeter of the elastic layer element and comprehending coextensive portions of the bodyside liner layer and the outer cover layer of the absorbent article, the outer cover layer being gathered when the bodyside liner layer and the elastic layer element are both substantially fully extended and substantially unstressed, such that the elastic layer and the bodyside liner layer are extensible with corresponding extension of gathers in the outer cover layer; the extensible zone being extensible in at least one of the first direction and the second cross direction, the extensible zone allowing a broad range of extensibility of the absorbent article by extension and retraction of the absorbent article in the at least one extensible zone. The outer cover layer is free from attachment to the elastic layer element in the extensible zone inwardly of the first outer perimeter of the absorbent article. The nonextensible material of the outer cover layer may comprise a woven or nonwoven fibrous web sufficiently nonextensible to substantially prevent extension when a force is applied thereto.

In another aspect of the invention, the absorbent article can be free from leg elastics and from waist elastics. This is because of the increased extensibility and retraction due to the extensible zones created in the absorbent article.

Another aspect of the invention comprises a method for forming an absorbent article having a length and a width, a front portion, a rear portion and a crotch portion connecting the front and rear portions, and a longitudinal axis extending through the front, rear and crotch portions and defining a first direction in the absorbent article aligned with the longitudinal axis and a respective second cross direction, the absorbent article containing at least one extensible zone, the method comprising forming a base structure extending substantially the entire length and the width of the absorbent article by attaching together an extensible bodyside liner layer and an extensible outer cover layer having at least the respective length and width; and creating the resiliently extensible zone in the base structure by incorporating at least one elastic layer element between the outer cover layer and the bodyside liner layer at the locus of the extensible zone, all of the elastic layer, the bodyside liner layer, and the outer cover layer being amenable to simultaneous coexistence in a substantially fully extended and substantially unstressed condition, whereby the absorbent article is formed with the extensible zone which allows a broad range of extensibility of the absorbent article within the extensible zone, by extension and retraction of the absorbent article in at least one extensible zone.

The method can further comprise attaching an absorbent core to the base structure, preventing extensibility of the absorbent article in an area controlled by the attachment of the absorbent core to the base structure.

The method can further include forming a nonextensible region of the absorbent article coextensive with the elastic layer by securing a substantially nonextensible layer element to the base structure in the nonextensible region so defined; whereby extension of the absorbent article in the nonextensible region is substantially restricted by the nonextensible layer.

The extensible outer cover layer and/or the extensible bodyside liner can comprise a necked nonelastic material formed by the step of applying a tensioning force to the nonelastic material whereby the tensioning force stretches the nonelastic material about 25% to about 150% in the first direction, and correspondingly narrows the nonelastic material in the cross direction. The extensible outer cover layer and the bodyside liner layer can both comprise necked nonelastic materials formed by applying a tensioning force to the neckable nonelastic material of both the outer cover layer and the bodyside liner layer to concurrently neck both materials, the necking narrowing both of the materials in the cross direction; and after necking both materials, creping both materials in the first direction, whereby the absorbent article is extensible in at least one extensible zone in both the first direction and the second cross direction.

In another aspect the invention comprises an absorbent article having a front portion, a rear portion, a crotch portion connecting the front and rear portions, and a longitudinal axis extending through the front, rear and crotch portions and defining a first direction of the absorbent article aligned with the longitudinal axis and a respective second cross direction, the absorbent article comprising an outer cover layer formed by a first material extensible in at least one of the first direction and the second cross direction; a bodyside liner layer formed by a second material extensible in at least one of the first direction and the cross direction, the bodyside liner layer and the outer cover layer forming, in combination, a base structure; and at least one extensible zone, comprehending coextensive portions of at least the bodyside liner layer and the outer cover layer, the extensible zone allowing a broad range of extensibility of the absorbent article within the extensible zone by extension of the absorbent article in the at least one extension zone. When the extensible zone is formed by the bodyside liner layer and the outer cover layer, the absorbent article is retractable in the extensible zone from about 5% to about 70% of a distance the base structure is extended. When the extensible zone further includes an elastic layer, the absorbent article is retractable in the extensible zone from about 70% to about 100% of a distance the base structure is extended. The at least one extensible zone can comprise a plurality of extensible zones, at least a first one of the extensible zones including an elastic layer, and at least a second one of the extensible zones being devoid of an elastic layer.

Figure 1:
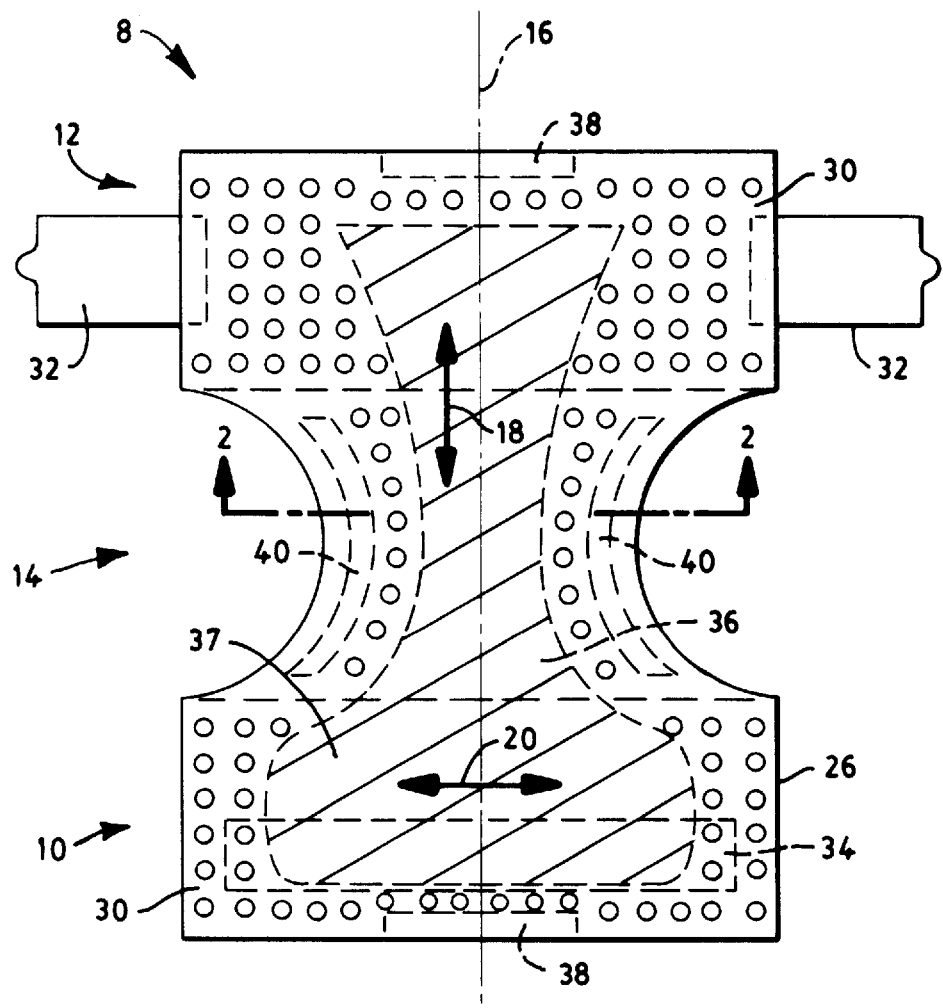
FIG. 1 illustrates a top view of a first embodiment of the invention.

The invention is not limited in its application to the details of construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE PREFERRED EMBODIMENTS

The present invention relates to absorbent articles designed to absorb body exudates. While the preferred embodiments of the present invention are described herein in terms of an absorbent article such as a diaper for an infant, the invention includes, and is equally applicable to, adult incontinent briefs, training pants and the like.

The present invention can best be understood by reference to the drawings. FIG. 1 illustrates an absorbent article 8 with a front portion 10, a rear portion 12, and a crotch portion 14 connecting the front portion 10 and the rear portion 12. The absorbent article 8 has a longitudinal axis 16 extending through the front, rear and crotch portions 10, 12, 14. The longitudinal axis 16 defines a first direction 18 aligned therewith and a respective cross direction 20 which is substantially perpendicular to the first direction 18. Directions 18 and 20 are indicated in FIG. 1 by arrows so labelled.

Figure 2:
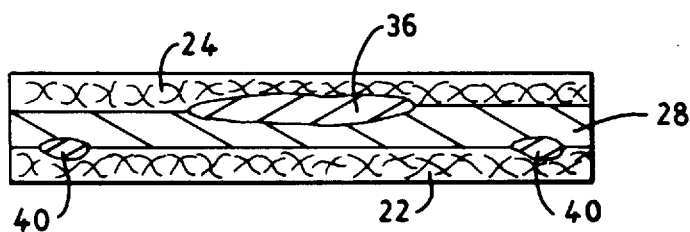
FIG. 2 illustrates a cross-sectional view of the absorbent article taken at 2—2 of FIG. 1 .

As shown in FIG. 2 which is a cross section taken along the line 2—2 of FIG. 1, the absorbent article 8 is formed by an outer cover layer 22 and a bodyside liner layer 24 which, in combination, comprise a base structure 26. An elastic layer 28 is mounted between the outer cover layer 22 and bodyside liner layer 24 to form extensible zones. The elastic layer 28 extends, from a rest disposition, with the outer cover layer 22 and the bodyside liner layer 24 when the outer cover layer 22 and the bodyside liner layer 24 are extended. Extending the elastic layer 28 creates retractive forces in the elastic layer 28. The retractive forces urge retractive restoration of the elastic layer 28 and extensible zone of absorbent article toward, and substantially to, its pre-extension dimensions.

The extensible zones comprise panels or regions of the absorbent article 8. In FIG. 1 and throughout the drawings, the extensible zones, as generally indicated at 30, are represented by circles which indicate the zone 30 is extensible in at least one direction. The extensible zones 30 are integral with the absorbent article 8, to the extent the zones 30 are formed with elements already present in the absorbent article.

Attachment elements 32 can comprise mechanical fasteners such as the hooks of a hook and loop fastening system attached to outer cover layer 22 on the rear portion 12 of the absorbent article 8 as shown in FIG. 1. A corresponding loop material or surface 34 is attached to the outer cover layer 22 on the front portion 10 and adapted to releasably engage with the hook material of the attachment elements 32. Other well known fastening means can also be used to support the absorbent article 8 upon a person. For example, a cohesive system, an adhesive fastener system or the like may also be utilized to fasten the absorbent article 8. An absorbent core 36 is also supported or mounted between the outer cover layer 22 and the bodyside liner layer 24.

The outer cover layer 22 comprises a first material preferably extending over substantially the entirety of the overall area of the absorbent article 8, and capable of being stretched in the first direction 18 increasing the length thereof, while being narrowed in the cross direction 20. Such materials include knitted and loosely woven fabrics, bonded carded webs, spunbonded webs and meltblown webs. A meltblown web typically includes meltblown microfibers. The material may also have multiple layers such as, for example, multiple spunbonded layers and/or meltblown layers. The material may be made of polymers such as, for example, polyolefins. Exemplary polyolefins include polypropylene, polyethylene, ethylene copolymers and propylene copolymers. See U.S. Pat. No. 5,226,992 to Morman et al., hereby incorporated by reference in its entirety, for teaching various materials which can form the outer cover layer 22. A preferred material for the outer cover layer 22 can comprise an extensible film laminated to a necked nonwoven spunbonded material. This nonwoven material should be extensible by 5% to 75%, preferably 10% to 50%, of its original length e.g. in the first direction 18 while correspondingly narrowed in the cross direction 20 due to the necking of the material by 5% to 75% of its original width.

The bodyside liner layer 24 comprises a second material preferably extending over substantially the entirety of the overall area of the absorbent article 8, and can be the same materials disclosed with respect to the outer cover layer 22 which are set forth in U.S. Pat. No. 5,226,992. A preferred material is a neck stretched spunbonded layer narrowed in the cross direction 20 by extending in a first direction 18 from 5% to 75% of its original length due to a force necking the material (See especially FIGS. 2, 2A and 2B of U.S. Pat. No. 5,226,992).

The elastic layer 28 can comprise a thermoplastic film or sheet of material made from block copolymers having a polymer endblock which contains a styrenic moiety and an elastic polymer midblock such as a conjugated diene or a lower alkene polymer. The elastic layer may be formed with, for example, a film of styrene/ethylene/butylene/styrene block copolymer available from the Shell Chemical Co. as KRATON® G. The elastic layer 28 may also comprise a film substantially impervious to liquids, strands of elastic material, elastic foams, or elastic adhesive coatings.

The extensible zones 30 comprise regions of the absorbent article where the outer cover layer 22 is attached to the bodyside liner layer 24 with the elastic layer 28 therebetween to form a composite multiple layer structure, and wherein each layer of the multiple layer structure is permissively extensible, such that the absorbent article 8 is stretchable in the extensible zone 30 in at least one direction. Alternatively, the outer cover layer 22, bodyside liner layer 24, and elastic layer 28 may be positioned in any arrangement to form the extensible zones 30. For example, the outer cover layer 22 may be positioned between the elastic layer 28 and the bodyside liner layer 24 to provide the extensible zones 30. Moreover, the bodyside liner layer 24, outer cover layer 22 and elastic layer 28 can simultaneously coexist in a substantially fully extended unstressed condition. This relationship is contemplated because no significant stress is placed upon the respective layers at the time the extensible zone 30 is formed.

The absorbent core 36 may suitably comprise a matrix of hydrophilic fibers, such as a web of cellulosic fluff, in combination with a high-absorbency material commonly known as superabsorbent material. In a particular embodiment, absorbent core 36 comprises a mixture of superabsorbent hydrogel-forming particles and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent core 36.

Alternatively, the absorbent core 36 may comprise a laminate of fibrous webs and superabsorbent material or other suitable means of maintaining a superabsorbent material in a localized area.

The absorbent core 36 may have any of a number of shapes. For example, the absorbent core 36 may be rectangular, I-shaped or T-shaped. It is generally preferred that the absorbent core 36 be narrower in the crotch portion 14 than in the rear portion 12 or front portion 10.

The high-absorbency material in the absorbent core 36 can be selected from natural, synthetic and modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

In FIG. 2, absorbent core 36 is shown mounted between bodyside liner layer 24 and elastic layer 28. While this arrangement is preferred, absorbent core 36 can also be mounted between elastic layer 28 and outer cover layer 22 providing the elastic layer 28 is sufficiently permeable to liquids to pass such liquids therethrough to the absorbent core 36. Of course, in some areas of the absorbent article 8, the elastic layer 28 may not be present between the outer cover layer 22 and the bodyside liner layer 24.

In the first embodiment of FIG. 1, the absorbent core 36 is fixed to the base structure 26 to form a nonextensible area 37 defined by the area over which the absorbent core 36 is effectively attached to the base structure 26. This nonextensible area 37 is shown by cross hatching. Other nonextensible regions are similarly shown by cross hatching of the absorbent core 36 and by an absence of circles or cross hatching in other parts of the structure, in others of the top view drawings.

Figure 5:
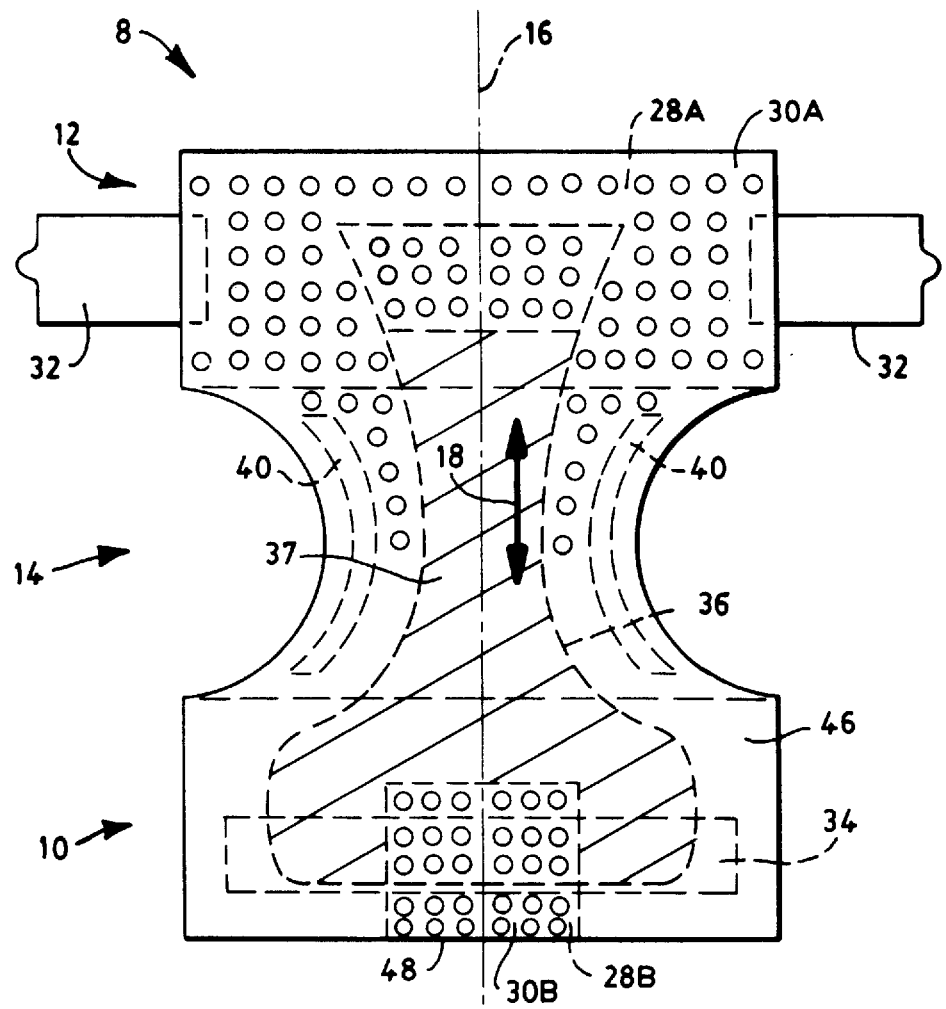
FIG. 5 illustrates a top view of a third embodiment of the invention.
Figure 9:
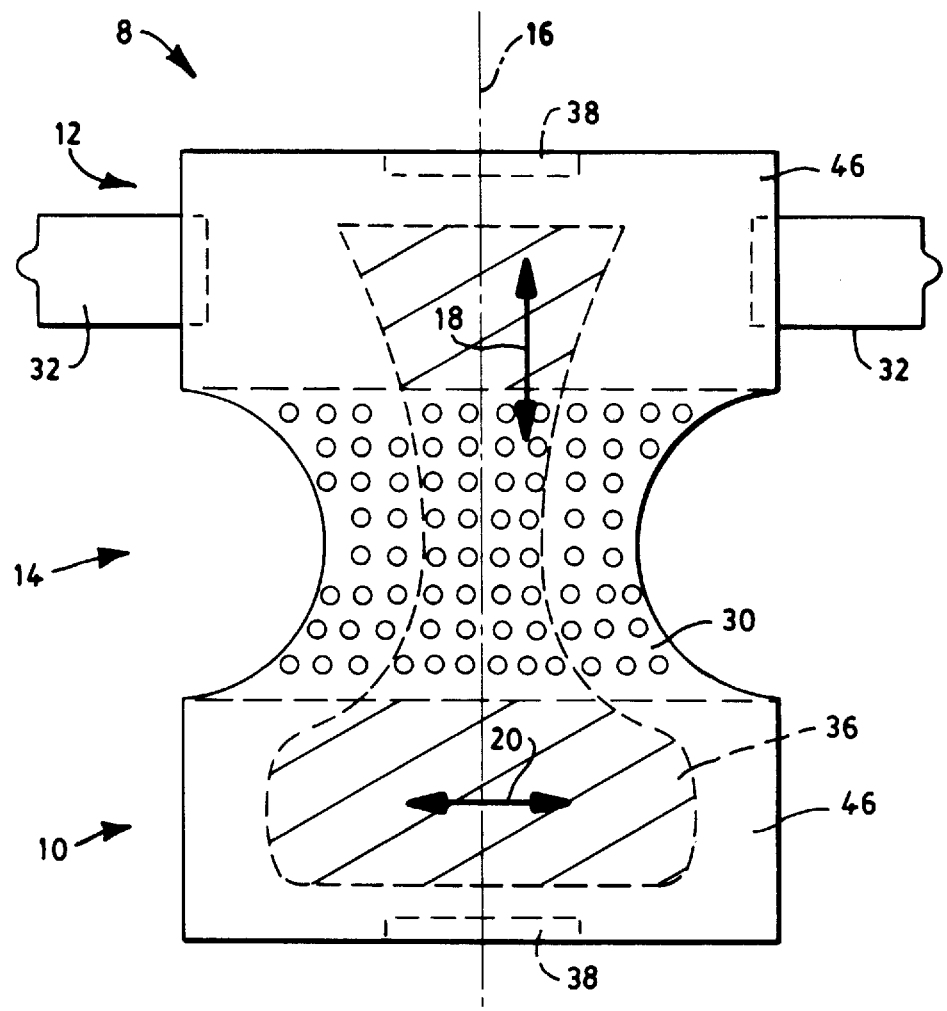
FIG. 9 illustrates a top view of a seventh embodiment of the invention.

In any area of the drawings in which the absorbent core 36 is not secured to the base structure 26, and elastic layer 28 is secured between bodyside liner layer 24 and outer cover layer 22, the region is marked with circles indicating an extensible zone 30. Front and rear waist elastics 38 and leg elastics 40 are also shown in FIG. 1. These elastics also enable the absorbent article 8 to fit a broad range of users. The leg elastics 40 may be formed from separate materials which are attached to the outer cover layer 22 and/or the bodyside liner 24. Materials suitable for forming leg elastics 40 or waist elastics 38, include strands, ribbons or one or more layers of a polymeric and/or elastic material which may be adhered to the absorbent article 8 while in a stretched position. The waist elastics 38 and/or the leg elastics 40 shown throughout the drawings are optional. If the extensible zones 30 cover a sufficient area of the absorbent article 8 and are sufficiently extensible in the first direction 18, the leg elastics 40 are not required as shown in FIG. 9. If the extensible zones 30 cover a sufficient area of the absorbent article 8 and are sufficiently extensible in the cross direction 20, the rear waist elastics 38 may not be required as shown in FIGS. 3 and 5.

Figure 3:
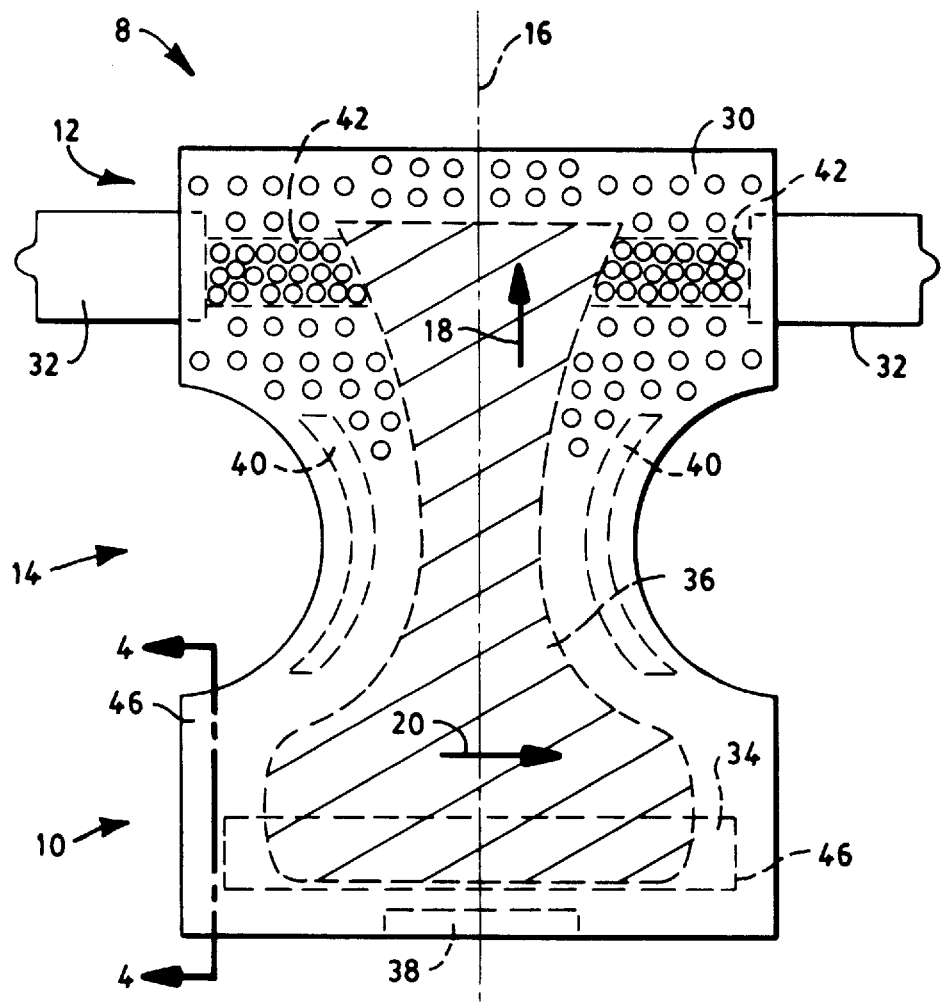
FIG. 3 illustrates a top view of a second embodiment of the absorbent article including additional elastics.

FIG. 3 shows a second embodiment, derived from the embodiment of FIG. 1. In this embodiment additional elastics 42 are provided in the rear portion 12 between the attachment elements 32 and the absorbent core 36, preferably not attached to absorbent core 36. These added elastics increase the ability of the rear portion 12 to extend and retract in the cross direction 20. This arrangement makes waist elastics 38 in the rear portion 12 of the absorbent article 8 less important. Further, as shown in FIG. 3, an area 46, devoid of both circles and cross hatching in the front portion 10 of the absorbent article 8, in the region of loop material or surface 34, is generally nonextensible.

Figure 4:
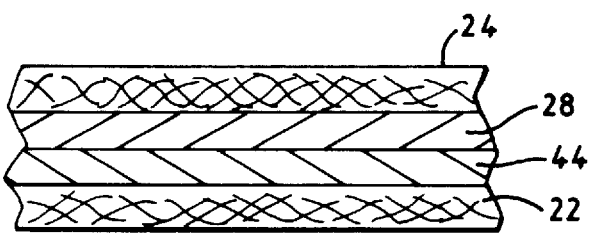
FIG. 4 illustrates a cross-sectional view of the absorbent article taken at 4—4 of FIG. 3 .

A fully extended, and otherwise nonextensible layer 44 can control the nonextensibility of this nonextensible area 46 as shown in FIG. 4 which is a cross-sectional view taken at 4—4 in FIG. 3. The nonextensible layer 44 preferably is attached over the entirety of its respective opposing surface to the outer cover layer 22 and the elastic layer 28 as shown in FIG. 4. The nonextensible layer 44 can also comprise a number of nonextensible layer elements attached to various portions of the absorbent article 8. There is no criticality to the location of the nonextensible layer 44 with respect to placement between the various other layers. The nonextensible layer 44 can be located between the bodyside liner layer 24 and the elastic layer 28 or can be attached only to the outer cover layer 22 or the bodyside liner layer 24.

The nonextensible layer 44 can comprise a polyethylene film or a polyethylene film laminated to a surface of a nonwoven web, such as a spunbonded web of polyolefin fibers. Further, the nonextensible layer 44 may be formed of a woven or nonwoven fibrous web or any other material sufficiently nonextensible to prevent substantial extension of the base structure 26 when attached thereto. In general, extensibility of this absorbent article 8 in the nonextensible area 46 is limited to 20% or less, of the unstretched dimension, in any direction.

The elastic layer 28 need not be present in the nonextensible area 46. Preferably the nonextensible layer 44 is used, or a number of nonextensible layer elements may be used, even in the absence of the elastic layer 28, since the base structure 26 does have some extensibility of its own as will be discussed later.

FIG. 5 illustrates a third preferred embodiment of the invention wherein substantially the entire rear portion 12 of the absorbent article 8 and optionally part of the crotch portion 14 comprise a first extensible zone 30A. Within a significant part of the rear portion 12, the absorbent core 36 is not fixed to the base structure 26. The absorbent core 36 is retained by a flap (not shown) or received without securement between the bodyside liner layer 24 and the elastic layer 28 in the rear portion 12. As illustrated by cross hatching, the absorbent core 36 is fixedly attached to the base structure 26 in crotch portion 14, in front portion 10, and in a minor part of rear portion 12.

The front portion 10 of the absorbent article 8 in FIG. 5 includes a nonextensible area 46 wherein the nonextensibility is controlled by a nonextensible material 44 substantially as set forth with respect to the front portion 10 of the absorbent article in FIG. 3. The embodiment of FIG. 5 optionally does not require rear waist elastics 38, and none are shown, because of the extensibility of the absorbent article 8 in extensible zone 30A in the cross direction 20 in rear portion 12.

A second extensible zone 30B is located in the front portion 10 of the absorbent article 8. The extensible zone 30B has a generally rectangular shape and extends from a central region across a front edge 48 of the front portion 10 inwardly into the front portion 10, and is superimposed over part of the absorbent core 36. The absorbent core remains fixedly attached to the base structure 26 in those areas on either side of the extensible zone 30 in the front portion 10, but not in the area of second extensible zone 30B. The nonextensible area 46 preferably includes separate nonextensible layer elements on either side of the extensible zone 30B in the front portion 10 of the absorbent article 8. Due to the ability of the extensible zone 30B to extend in the cross direction, the embodiment of FIG. 5, as shown, may require no front or rear waist elastics 38, 40. The extensible zones 30A, 30B are formed by elastic layer elements, having an outer perimeter defined by elastic layer elements 28A, 28B for each of the respective extensible zones.

Figure 6:
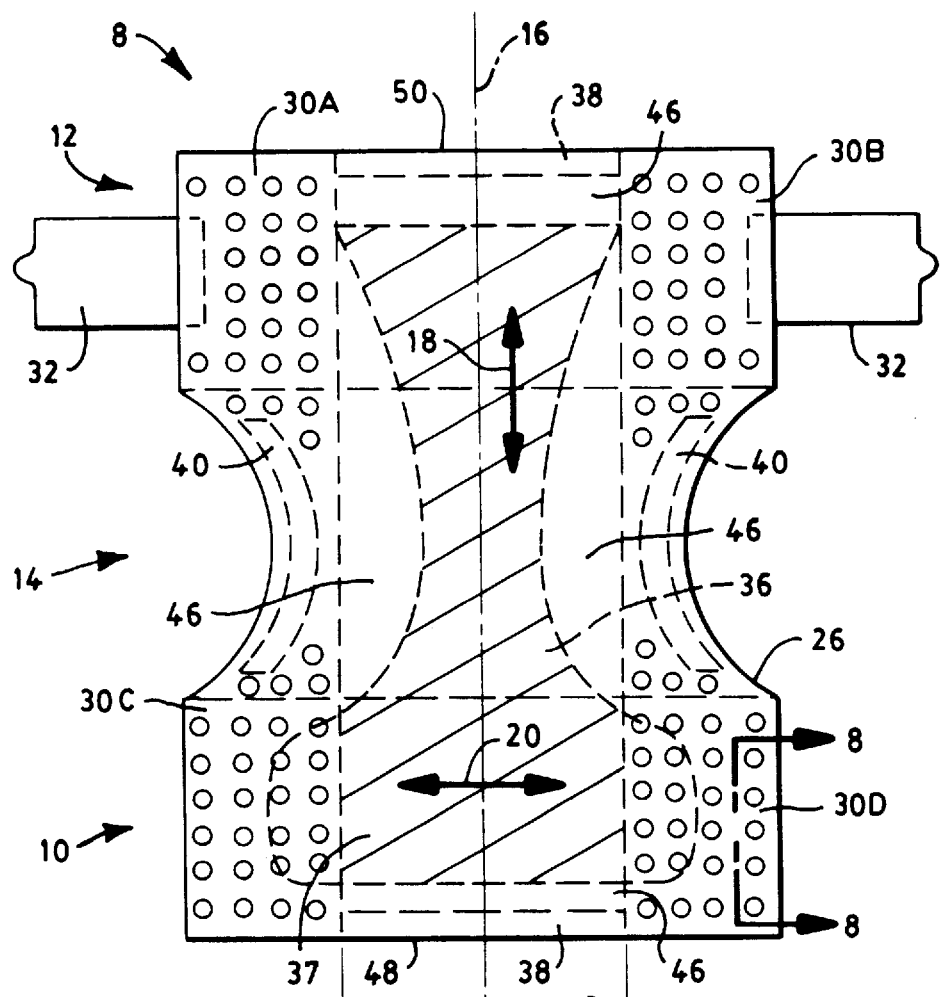
FIG. 6 illustrates a top view of a fourth embodiment of the invention.

The embodiment of FIG. 6 includes extensible zones 30A, 30B, 30C, 30D on opposing sides of the absorbent article 8 in the respective front portion 10 and rear portion 12. The absorbent article 8 is not extensible in a central nonextensible area 46 which extends the length of the absorbent article 8, from front edge 48 to rear edge 50 of rear portion 12, the nonextensible area 46 extending along the longitudinal axis 16 and having a width "W1" narrower than the minimum width of the absorbent article 8 at the crotch portion 14 thereof. This embodiment preferably includes elastic layer elements, defined by the elastic layer 28, for each of the extensible zones 30A, 30B, 30C, 30D. This embodiment preferably includes a nonextensible layer or layers 44, or corresponding nonextensible layer elements, which limit extensibility in nonextensible area 46 of the absorbent article. The absorbent core 36 is supported by the base structure 26 at outer surfaces of the absorbent core 36, but is unattached to the base structure 26 in the front portion 10 of the absorbent article 8.

Figure 7:
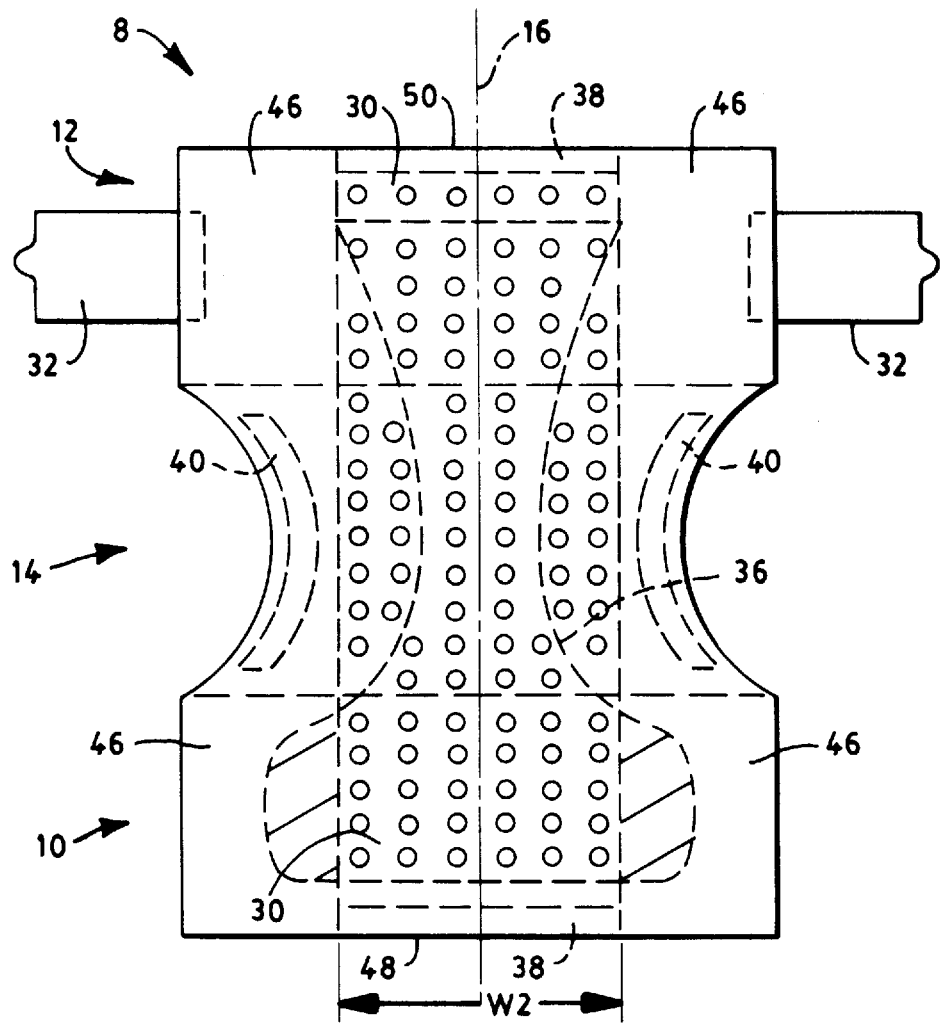
FIG. 7 illustrates a top view of a fifth embodiment of the invention.

In the embodiment of FIG. 7 extensible zones 30 and nonextensible areas 46 are substantially the reverse of the respective zones 30 and areas 46 in the embodiment of FIG. 6. The central area of the absorbent article 8 forms a central extensible zone 30 extending along the length of the absorbent article 8 from front edge 48 to rear edge 50, the extensible zone 30 extending along the longitudinal axis 16 and having a width "W2" narrower than, but covering the bulk of, the minimum width of the absorbent article 8 at the crotch portion 14. The absorbent core 36 is received without securement to the outer cover layer 22 or the bodyside liner layer 26 in the extensible zone 30. Thus, the absorbent core 36 is unattached to outer cover layer 22 and bodyside liner layer 26 within the crotch portion 14 and rear portion 12 of the absorbent article. The absorbent core 36 is secured to at least one of the outer cover layer 22 and the bodyside liner layer 26 at outside elements of the front portion 10. The absorbent core 36 is retained by a flap (not shown) or otherwise unattached or supported without securement between the bodyside liner layer 24 and the elastic layer 28 in the rear portion 12 and crotch portion 14 as described earlier.

As described earlier, the extensible zones 30 generally comprise regions of the absorbent article wherein at least one of the outer cover layer 22 and the bodyside liner layer 24 is attached to the elastic layer 28 such that the absorbent article 8 is resiliently stretchable in the extensible zone 30 in at least one direction. The bodyside liner layer 24, outer cover layer 22 and elastic layer 28 can simultaneously coexist in a substantially fully extended unstressed condition (untensioned). This relationship is contemplated because typically no significant stress is placed upon the layers 22, 24, 28 when the respective layers are secured to each other.

Critical in this invention is the concept that at least one layer of the base structure can be extended in at least one direction beyond its fully extended unstressed condition by applying extending forces such that the base structure embodies an extended stressed condition having a greater length in the at lest one direction than the base structure in its fully extended unstressed condition. In some embodiments, the layer is extendible in a second perpendicular or cross direction. A variety of methods can be used for providing extensibility in the second cross direction 20.

Figure 8:
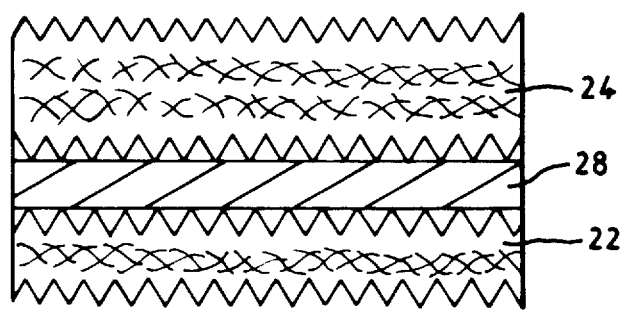
FIG. 8 illustrates a cross-sectional view taken representationally at 8—8 of FIG. 6 and showing a sixth embodiment in which the absorbent article is extensible in two directions.

FIG. 8 shows a cross-sectional view taken at 8—8 in FIG. 6. FIG. 8 is not per se representing the embodiment of FIG. 6. FIG. 8 represents an embodiment of the invention wherein the extensible zones 30 are extensible in both the first direction 18 and the second cross direction 20. The two direction stretching in FIG. 8, and especially stretching in the first longitudinal direction 18, is enabled by creping or other foreshortening processes on either or both of the bodyside liner layer 24 and outer cover layer 22 such that the creped respective layers are extensible in the first direction 18. In such case, the absorbent article 8 can stretch, in extensible zones 30 in both the first direction 18 (as a result of the creping) and the cross direction 20 (as a result of the necking). Preferably microcreping is utilized to make the materials of the base structure 26 sufficiently extensible in the first direction 18.

The multi-directional stretching arrangement of FIG. 8 can be applied to all of the examples herein disclosed. In the embodiment of FIG. 9 such an arrangement can accommodate removal of leg elastics 40 because of the elasticity of the extensible zone 30 in the crotch portion 14.

The embodiment of FIG. 9 shows an absorbent article 8 with longitudinal extensibility in the crotch portion 14. The crotch portion 14 comprises an extensible zone 30 extensible in the first direction 18. The absorbent core 36 is preferably fixedly attached to the base structure 26 in only the front portion 10 of the absorbent article 8. The absorbent core 36 is received without securement between the outer cover layer 22 and the bodyside liner layer 24 in the rear portion 12 and crotch portion 14. In this embodiment no leg elastics 40 are required because of the longitudinal extensibility of the extensible zone 30 in the crotch portion 14. This increased longitudinal extensibility allows the absorbent article 8 to fit a wider range of users.

The embodiment of FIG. 9, may of course, employ nonelongated leg elastics. Such nonelongated leg elastics provide additional retractive tension in the crotch portion 14 of the absorbent article 8, if additional restorative force is required. Unstressed leg elastics, when used, are spaced outwardly from the longitudinal axis 16, the unstressed elastics stretching when the extensible zone 30 stretches in the first direction 18 increasing the overall length of the absorbent article 8.

In another embodiment, the outer cover layer 22 comprises a substantially nonextensible material. This nonextensible material can comprise a material such as a woven or nonwoven fibrous web or any other material sufficiently nonextensible to substantially prevent extension when a force is applied thereto. However, in the assembled absorbent article 8, the outer cover layer 22 is gathered when the elastic layer 28 and the bodyside liner layer 24 are both substantially fully extended and substantially unstressed. In this arrangement the bodyside liner layer 24 and elastic layer 28 are extensible with corresponding extension of the gathers in the outer cover layer 22, but not beyond the fully extended dimensions of the outer cover layer 22, over the area where the outer cover layer 22 is effectively attached to either or both of the elastic layer 28 and the bodyside liner layer 24.

This embodiment pictorially is the same as those shown in FIGS. 1, 3, 5–7 and 9. The only difference is the outer cover layer 22 is nonextensible, oversized, and gathered to allow the bodyside liner layer 24 and elastic layer 28 to extend and retract all while the outer cover layer 22 is no more than fully extended without stress on the fibers or other elements forming the outer cover layer 22. The forces or elements (e.g. creping or elastic strands) which cause the gathering are, of course, stressed, if even modestly, in relaxation of the gathers as the outer cover layer 22 is extended, potentially to its fully extended, but substantially unstretched condition.

In some embodiments of the invention, at least one extensible zone 30 of the absorbent article 8 does not include an elastic layer 28. This zone, or zones 30, is extensible in at least one direction. The zones 30 devoid of elastic layer 28 do not, however, have the same amount of retractability as the zones 30 which include an elastic layer 28. Extensible zones 30 with elastic layer 28 have an ability to retract after stretching by between about 70% and about 100% of the amount stretched. Extensible zones 30 without elastic layer 28 have an ability to retract between about 5% and about 70%, but preferably between 5% and about 50% of the stretched amount (i.e. a distance the zone 30 is extended). The extension is defined as the increased length or extension caused by stretching in the extensible zone 30. Therefore, with respect to the embodiments previously disclosed, the extensible zones or portions thereof may comprise extensible zones 30 without an elastic layer 28. Extensible zones 30 without an elastic layer 28 are extensible, but less retractable than areas with the elastic layer 28. Namely, the elastic layer 28 generally provides the bulk of the retractive forces in the extensible zones 30. Extensible zones 30 can be formed by a material which when placed under tension expands or extends by about 10% to about 200% from its original dimension. Therefore, there is great variation in the amount of extensibility of extensible zones 30 depending upon the type of material used, and the arrangement of the material.

While not specifically disclosed, any combination of the elements shown in FIGS. 1–9 and a wide variety of variations thereon is contemplated. For example, any embodiment shown may include or exclude either waist elastics 38 and/or leg elastics 40. Also, any embodiment shown may include extensible zones 30 with an elastic layer 28 and/or extensible zones 30 without an elastic layer 28.

The invention disclosed improves the fit of an absorbent article 8 upon the user. For example, both waist circumference and thigh circumference may vary by 1–2 inches in the same infant depending upon the disposition of the infant, for example sitting versus standing. Rise variations can be 1 inch in the same baby depending on whether sitting or standing. This invention improves the fit of an absorbent article 8 and the size range of users upon which the absorbent article 8 will fit.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

Having thus described the invention, what is claimed is:

1. An absorbent article having a front portion, a rear portion, and a crotch portion connecting said front and rear portions, and a first outer perimeter, said front portion, said rear portion, and said crotch portion, in combination, defining an overall area of said absorbent article, a longitudinal axis extending through said front, rear and crotch portions and defining a first direction in said absorbent article aligned substantially with said longitudinal axis and a respective second cross direction, said absorbent article comprising:

(a) an outer cover layer formed by a first material extensible in at least one of the first direction and the second cross direction;

(b) a bodyside liner layer formed by a second material extensible in at least one of the first direction and the second cross direction, said bodyside liner layer and said outer cover layer being secured to said absorbent article, and forming, in combination, a base structure;

(c) at least one elastic layer having a second outer perimeter, said elastic layer being located between said outer cover layer and said bodyside liner layer, and attached to at least one of said outer cover layer and said bodyside liner layer, wherein said outer cover layer, said bodyside liner layer, and said elastic layer can simultaneously coexist in a substantially fully extended unstressed condition;

(d) an absorbent secured to said absorbent article; and (e) at least one extensible zone, defined within the second outer perimeter of said at least one elastic layer and comprehending coextensive portions of said bodyside liner layer and said outer cover layer, said at least one extensible zone allowing a broad range of extensibility of said absorbent article within said at least one extensible zone by extension and retraction of said absorbent article in said at least one extensible zone.

2. An absorbent article of claim 1, further comprising an attachment element located in said rear portion of said absorbent article, said attachment element cooperating in securing said absorbent article upon a user, said attachment element extending outwardly from respective edges of said rear portion of said absorbent article, said at least one extensible zone being located in said rear portion of said absorbent article adjacent to and extending inwardly from said attachment element.

3. An absorbent article of claim 1, said absorbent including a nonextensible absorbent core between said bodyside liner layer and said elastic layer, said base structure being effectively fixedly attached to said absorbent core over an area of said base structure whereby said base structure is not extensible over the respective area of said base structure controlled by the attachment between said absorbent core and said base structure.

4. An absorbent article of claim 1 wherein said second extensible material of said bodyside liner layer comprises a spunbonded layer stretched in one of the first direction and the second cross direction by about 5% to about 75%, and correspondingly narrowed in the other of the first direction and the second cross direction.

5. An absorbent article of claim 1 wherein said first extensible material of said outer cover layer comprises a spunbonded layer stretched in one of the first direction and the second cross direction by about 5% to about 75%, and correspondingly narrowed in the other of the first direction and the second cross direction.

6. An absorbent article of claim 1 wherein said first extensible material of said outer cover layer is selected from one or more of the group consisting of a spunbonded material, a spunbonded laminate material, and a bonded carded web.

7. An absorbent article of claim 1 wherein both of said first and second extensible materials, of both said bodyside liner layer and said outer cover layer, have been narrowed in the second cross direction, by stretching in the first direction and corresponding necking in the second cross direction, said at least one extensible zone being extensible in the second cross direction.

8. An absorbent article of claim 7 wherein both said bodyside liner layer and said outer cover layer are creped such that the creping is extensible in the first direction, such that said absorbent article is extensible in said at least one extensible zone in both the first direction and the second cross direction.

9. An absorbent article of claim 1 wherein said absorbent article is extensible, in said at least one extensible zone, in the second cross direction.

10. An absorbent article of claim 1 wherein said elastic layer is disposed only in common with the respective said at least one extensible zone.

11. An absorbent article of claim 1 wherein said elastic layer comprises a sheet of elastic material.

12. An absorbent article of claim 1 wherein said absorbent comprises an absorbent core and said base structure is effectively attached to said absorbent core over an area of said base structure whereby said base structure is not extensible over the respective area of said base structure controlled by the attachment between said absorbent core and said base structure, the remainder of said base structure being extensible and comprising said at least one extensible zone.

13. An absorbent article of claim 1, including an attachment element mounted to said rear portion of said absorbent article, and securing said absorbent article to a user by securement of said attachment element to said front portion, said absorbent comprising an absorbent core, and said base structure being attached to said absorbent core and attached to a nonextensible layer element in a region of said front portion of said absorbent article adjacent securement of said attachment element to said front portion of said absorbent article.

14. An absorbent article of claim 13, said at least one extensible zone comprising first and second extensible zones, said attachment element comprising a first attachment element, and a second attachment element, said respective first and second attachment elements being disposed on opposing sides of said rear portion and adjacent said first and second extensible zones, said rear portion of said absorbent article including a second elastic layer in said second extensible zone, said first and second elastic layers being disposed between respective ones of said attachment elements and said absorbent core.

15. An absorbent article of claim 1, said absorbent article comprising a respective said extensible zone in said rear portion and in said crotch portion, said base structure thereby having extensible properties in said rear portion, and in said crotch portion adjacent said rear portion and extending to a narrowest part of said crotch portion, said absorbent comprising an absorbent core disposed between said outer cover layer and said bodyside liner layer and extending from within said front portion, through said crotch portion to within said rear portion, said absorbent core being free from fixed attachment to said base structure over a substantial area of said rear portion of said absorbent article, coextensive with said absorbent core, whereby said base structure is extensible in said rear portion independent of said absorbent core.

16. An absorbent article of claim 15, including a respective said extensible zone in said front portion of said absorbent article, said second extensible zone extending from a central region across a front edge of said front portion inwardly into said front portion.

17. An absorbent article of claim 1 wherein said base structure is extensible in respective said extensible zones on opposing sides of said absorbent article in said front portion and said rear portion of said absorbent article, said absorbent article not being extensible in a central region of said absorbent article extending along the longitudinal axis and having a width narrower than a minimum width of said absorbent article.

18. An absorbent article of claim 1 wherein said base structure is extensible in a respective said central extensible zone extending along the longitudinal axis and having a width narrower than a minimum width of said absorbent article, said absorbent including an absorbent core received between said outer cover layer and said bodyside liner layer, in said front portion, said crotch portion and said rear portion of said absorbent article, said absorbent core being without effective securement to either of said outer cover layer or said bodyside liner layer about said central extensible zone.

19. An absorbent article of claim 1 wherein said base structure is extensible in a respective said extensible zone comprising said crotch portion of said absorbent article.

20. An absorbent article of claim 19, said crotch portion including leg elastics spaced outwardly from said longitudinal axis, wherein said leg elastics can coexist simultaneously with said base structure in substantially fully extended unstressed condition, said leg elastics extending when said base structure is extended in said extensible zone in the first direction.

21. An absorbent article of claim 1 wherein said elastic layer extends between said outer cover layer and said bodyside liner layer over the overall area defined by said absorbent article.

22. An absorbent article of claim 21 wherein at least one substantially nonextensible layer element is attached to said base structure in at least one region outside respective said at least one extensible zone.

23. An absorbent article having a front portion, a rear portion, a crotch portion connecting said front and rear portions, and a longitudinal axis extending through said front, rear and crotch portions and defining a first direction of said absorbent article aligned with said longitudinal axis and a respective second cross direction, said absorbent article comprising:
(a) an outer cover layer formed by a first material extensible in at least one of the first direction and the second cross direction;
(b) a bodyside liner layer formed by a second material extensible in at least one of the first direction and the second cross direction, said bodyside liner layer and said outer cover layer being secured to said absorbent article, and forming, in combination, a base structure;
(c) an absorbent core disposed between said outer cover layer and said bodyside liner layer,
(d) at least one elastic layer comprising a sheet or film of elastic material having a second outer perimeter, said elastic layer being located between said outer cover layer and said bodyside liner layer, and attached to at least one of said outer cover layer and said bodyside liner layer, wherein said outer cover layer, said bodyside liner layer, and said elastic layer can simultaneously coexist in a substantially fully extended unstressed condition; and
(e) at least one extensible zone, comprehending coextensive portions of at least said bodyside liner layer and said outer cover layer,
said at least one extensible zone allowing a broad range of extensibility of said absorbent article within said at least one extensible zone by extension of said absorbent article in said at least one extension zone beyond a length or a width of said absorbent article in the substantially fully extended unstressed condition.

24. An absorbent article of claim 23 wherein said at least one extensible zone is formed by said bodyside liner layer and said outer cover layer, said absorbent article being retractable in said at least one extensible zone from about 5% to about 70% of a distance said base structure is extended.

25. An absorbent article of claim 23 wherein said at least one extensible zone further includes said elastic layer, said absorbent article being retractable in said at least one extensible zone from about 70% to about 100% of a distance said base structure is extended.

26. An absorbent article of claim 23 wherein said at least one extensible zone comprises a plurality of extensible zones, at least a first one of said extensible zones including said elastic layer, and at least a second one of said extensible zones being devoid of an elastic layer.

27. An absorbent article of claim 23 wherein said first extensible material of said outer cover is selected from one or more of the group consisting of a spunbonded material, a spunbonded laminate material, and a bonded carded web.

28. An absorbent article of claim 23 wherein both of said first and second extensible materials, of both said bodyside liner layer and said outer cover layer, have been narrowed in the second cross direction, by stretching in the first direction and corresponding necking in the second cross direction, said at least one extensible zone being extensible in the second cross direction.

29. An absorbent article of claim 28 wherein both said bodyside liner layer and said outer cover layer are creped such that the creping is extensible in the first direction, and wherein said absorbent article is extensible in said at least one extensible zone in both the first direction and the second cross direction.

30. An absorbent article of claim 23 wherein said absorbent article in said at least one extensible zone is extensible in the second cross direction.

31. An absorbent article of claim 23 wherein said base structure is effectively attached to said absorbent core, whereby said base structure is not extensible over an area of said base structure controlled by the attachment between said absorbent core and said base structure, the remainder of said base structure being extensible and comprising said at least one extensible zone.

32. An absorbent article of claim 23, including an attachment element mounted to said rear portion of said absorbent article, and securing said absorbent article to a user by securement of said attachment element to said front portion, said base structure being attached to said absorbent core and attached to a nonextensible layer element in a region of said front portion of said absorbent article adjacent securement of said attachment element to said front portion of said absorbent article.

33. An absorbent article of claim 23, said absorbent article comprising a respective said extensible zone in said rear portion and in said crotch portion, said base structure thereby having extensible properties in said rear portion, and in said crotch portion adjacent said rear portion and extending to a narrowest part of said crotch portion, said absorbent core extending from within said front portion, through said crotch portion, to within said rear portion, said absorbent core being free from fixed attachment to said base structure over a substantial area of said rear portion of said absorbent article, coextensive with said absorbent core, whereby said base structure is extensible in said rear portion independent of said absorbent core.

34. An absorbent article of claim 33, including a respective said second extensible zone in said front portion of said absorbent article, said second extensible zone extending from a central region across a front edge of said front portion inwardly into said front portion.

35. An absorbent article of claim 23 wherein said base structure is extensible in respective said extensible zones on opposing sides of said absorbent article in said front portion and said rear portion of said absorbent article, said absorbent article not being extensible in a central region of said absorbent article extending along the longitudinal axis and having a width narrower than a minimum width of said absorbent article.

36. An absorbent article of claim 23 wherein said base structure is extensible in a respective said central extensible zone extending along the longitudinal axis and having a width narrower than a minimum width of said absorbent article, said absorbent core being without effective securement to either of said outer cover layer or said bodyside liner layer about said central extensible zone.

37. An absorbent article of claim 23 wherein said base structure is extensible in a respective said extensible zone comprising said crotch portion of said absorbent article.

38. An absorbent article of claim 70, said crotch portion including leg elastics spaced outwardly from said longitudinal axis, wherein said leg elastics can coexist simultaneously with said base structure in substantially fully extended unstressed condition, said leg elastics extending when said base structure is extended in said extensible zone in the first direction, said leg elastics being generally unstressed when attached to said crotch portion of said absorbent article and stressed when said absorbent article is applied to a user.

39. An absorbent article of claim 23 wherein said absorbent article is free from leg elastics.

40. An absorbent article of claim 23 wherein said absorbent article is free from waist elastics.

41. An absorbent article of claim 1 wherein said absorbent article is free from leg elastics.

42. An absorbent article of claim 1 wherein said absorbent article is free from waist elastics.

43. An absorbent article of claim 1 wherein said elastic layer comprises a thermoplastic film.

44. An absorbent article having a front portion, a rear portion, a crotch portion connecting said front and rear portions, and a longitudinal axis extending through said front, rear and crotch portions and defining a first direction of said absorbent article aligned with said longitudinal axis and a respective second cross direction, said absorbent article comprising:

(a) an outer cover layer formed by a first material extensible in at least one of the first direction and the second cross direction;

(b) a bodyside liner layer formed by a second material extensible in at least one of the first direction and the second cross direction, said bodyside liner layer and said outer cover layer being secured to said absorbent article, and forming, in combination, a base structure;

(c) an absorbent core disposed between said outer cover layer and said bodyside liner layer, (d) at least one elastic layer having a second outer perimeter, said elastic layer being located between said outer cover layer and said bodyside liner layer, and attached to at least one of said outer cover layer and said bodyside liner layer, wherein said outer cover layer, said bodyside liner layer, and said elastic layer can simultaneously coexist in a substantially fully extended unstressed condition; and (e) at least one extensible zone, comprehending coextensive portions of at least said bodyside liner layer and said outer cover layer, said absorbent article being free from leg elastics, said at least one extensible zone allowing a broad range of extensibility of said absorbent article within said at least one extensible zone by extension of said absorbent article in said at least one extension zone beyond a length or a width of said absorbent article in the substantially fully extended unstressed condition.

45. An absorbent article of claim 44, said elastic layer comprising a sheet of elastic material.

46. An absorbent article of claim 44, said elastic layer comprising a thermoplastic film.

47. An absorbent article of claim 44, further comprising an attachment element located in said rear portion of said absorbent article, said attachment element cooperating in securing said absorbent article upon a user, said attachment element extending outwardly from respective edges of said rear portion of said absorbent article, said at least one extensible zone being located in said rear portion of said absorbent article adjacent to and extending inwardly from said attachment element.

48. An absorbent article of claim 44, said absorbent core being nonextensible, said base structure being effectively fixedly attached to said absorbent core over an area of said base structure whereby said base structure is not extensible over the respective area of said base structure controlled by the attachment between said absorbent core and said base structure.

49. An absorbent article of claim 44 wherein said absorbent article is extensible, in said at least one extensible zone, in the second cross direction.

50. An absorbent article of claim 44 wherein said elastic layer is disposed only in common with the respective said at least one extensible zone.

51. An absorbent article of claim 44, including an attachment element mounted to said rear portion of said absorbent article, and securing said absorbent article to a user by securement of said attachment element to said front portion, said base structure being attached to said absorbent core and attached to a nonextensible layer element in a region of said front portion of said absorbent article adjacent securement of said attachment element to said front portion of said absorbent article.

52. An absorbent article of claim 51, said at least one extensible zone comprising first and second extensible zones, said attachment element comprising a first attachment element, and a second attachment element, said respective first and second attachment elements being disposed on opposing sides of said rear portion and adjacent said first and second extensible zones, said rear portion of said absorbent article including a second elastic layer in said second extensible zone, said first and second elastic layers being disposed between respective ones of said attachment elements and said absorbent core.

53. An absorbent article of claim 44, said absorbent article comprising a respective said extensible zone in said rear portion and in said crotch portion, said base structure thereby having extensible properties in said rear portion, and in said crotch portion adjacent said rear portion and extending to a narrowest part of said crotch portion, said absorbent core being free from fixed attachment to said base structure over a substantial area of said rear portion of said absorbent article, coextensive with said absorbent core, whereby said base structure is extensible in said rear portion independent of said absorbent core.

54. An absorbent article of claim 53, including a respective said extensible zone in said front portion of said absorbent article, said second extensible zone extending from a central region across a front edge of said front portion inwardly into said front portion.

55. An absorbent article of claim 44 wherein said base structure is extensible in respective said extensible zones on opposing sides of said absorbent article in said front portion and said rear portion of said absorbent article, said absorbent article not being extensible in a central region of said absorbent article extending along the longitudinal axis and having a width narrower than a minimum width of said absorbent article.

56. An absorbent article of claim 44 wherein said base structure is extensible in a respective said central extensible zone extending along the longitudinal axis and having a width narrower than a minimum width of said absorbent article, said absorbent core being without effective securement to either of said outer cover layer or said bodyside liner layer about said central extensible zone.

57. An absorbent article of claim 44 wherein said base structure is extensible in a respective said extensible zone comprising said crotch portion of said absorbent article.

58. An absorbent article of claim 44 wherein said elastic layer extends between said outer cover layer and said bodyside liner layer over the overall area defined by said absorbent article.

59. An absorbent article of claim 44 wherein said absorbent article is free from waist elastics.

\* \* \* \* \*

UNITED STATES PATENT AND TRADEMARK OFFICE
CERTIFICATE OF CORRECTION

PATENT NO. : 5,846,232
DATED : Dec. 8, 1998
INVENTOR(S) : Paul J. Serbiak et al

It is certified that error appears in the above-identified patent and that said Letters Patent is hereby corrected as shown below:

On the title page, Inventors should read:

Paul John Serbiak, Appleton; Duane Girard Uitenbroek, Little Chute; Georgia Lynn Zehner, Larsen, all of Wis.

Signed and Sealed this

Sixth Day of April, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO. : 5,846,232
DATED : December 8, 1998
INVENTOR(S) : Paul John Serbiak et al.

It is certified that error appears in the above-identified patent and that said Letters Patent is hereby corrected as shown below:

In the Specification:
Column 1, line 37, change "user'body" to --user's body--.
Column 10, line 54, change "lest" with --least--.

In the Claims:
Claim 38, line 1, change "70" to --37--.

Signed and Sealed this

Sixth Day of February, 2001

Attest:

Q. TODD DICKINSON

*Attesting Officer*    *Director of Patents and Trademarks*